United States Patent [19]

Krishnan et al.

[11] Patent Number: 5,011,295
[45] Date of Patent: Apr. 30, 1991

[54] METHOD AND APPARATUS TO SIMULTANEOUSLY MEASURE EMISSIVITIES AND THERMODYNAMIC TEMPERATURES OF REMOTE OBJECTS

[75] Inventors: Shankar Krishnan, Arlington Heights, Ill.; George P. Hansen, Austin, Tex.; Robert H. Hauge, Houston, Tex.; John L. Margrave, Houston, Tex.; Charles A. Rey, Riverwoods, Ill.

[73] Assignee: Houston Advanced Research Center, The Woodlands, Tex.

[21] Appl. No.: 422,644

[22] Filed: Oct. 17, 1989

[51] Int. Cl.$^5$ .......................... G01J 5/58; G01J 5/10; G01K 7/00
[52] U.S. Cl. ........................................ 374/126; 374/9; 374/128; 374/124; 374/137
[58] Field of Search ................. 374/126, 128, 9, 121, 374/124, 137; 356/43, 45

[56] References Cited

U.S. PATENT DOCUMENTS

| | | | |
|---|---|---|---|
| 3,422,678 | 1/1969 | Murray | 374/126 |
| 3,462,224 | 8/1969 | Woods et al. | 374/126 |
| 3,492,869 | 2/1970 | Toyota et al. | 374/126 |
| 3,745,830 | 7/1973 | Smith, Jr. | 374/128 |
| 3,948,345 | 4/1976 | Rosencwaig | 374/128 |
| 4,360,723 | 11/1982 | Fukuda et al. | 374/128 |
| 4,561,786 | 12/1985 | Anderson | 374/128 |
| 4,708,493 | 11/1987 | Stein | 374/128 |
| 4,840,496 | 6/1989 | Elleman et al. | 374/126 |
| 4,919,542 | 4/1990 | Nulman et al. | 374/9 |

FOREIGN PATENT DOCUMENTS

| | | | |
|---|---|---|---|
| 0121728 | 5/1989 | Japan | 374/126 |
| 2101309 | 1/1983 | United Kingdom | 374/9 |

OTHER PUBLICATIONS

Hansen, G. P. et al., "Measurement of Temperature and Emmissivity of Speculary Reflecting Glowing Bodies", Met. Trans., vol. 19A (Aug. 1988).
Bernard, B., "Determining Emissivity", Instruments & Control Systems, vol. 37, No. 5 (May 1964).
"Radiation Pyrometry", Milletron Incorporated, Pittsburgh, PA (Oct. 1966).
Kampel, I. J., "A Yig Radiometer and Temperature Controller", Wireless World, vol. 76, No. 1420 (Oct. 1970).

*Primary Examiner*—William A. Cuchlinksi, Jr.
*Assistant Examiner*—Diego F. F. Gutierrez
*Attorney, Agent, or Firm*—Juettner Pyle & Lloyd

[57] ABSTRACT

Method and apparatus for accurately and instantaneously determining the thermodynamic temperature of remote objects by continuous determination of the emissivity, the reflectivity, and optical constants, as well as the apparent or brightness temperature of the sample with a single instrument. The emissivity measurement is preferably made by a complex polarimeter including a laser that generates polarized light, which is reflected from the sample into a detector system. The detector system includes a beamsplitter, polarization analyzers, and four detectors to measure independently the four Stokes vectors of the reflected radiation. The same detectors, or a separate detector in the same instrument, is used to measure brightness temperature. Thus, the instrument is capable of measuring both the change in polarization upon reflection as well as the degree of depolarization and hence diffuseness. This enables correction for surface roughness of the sample and background radiation, which could otherwise introduce errors in temperature measurement.

17 Claims, 7 Drawing Sheets

METHOD AND APPARATUS TO SIMULTANEOUSLY MEASURE EMISSIVITIES AND THERMODYNAMIC TEMPERATURES OF REMOTE OBJECTS

BACKGROUND OF THE INVENTION

This invention relates to methods and apparatus used for accurately measuring the temperature of remote objects by a non-contact method, and more particularly, to such a method and apparatus which can determine and correct for all critical variables, especially for surface imperfections, of such objects under investigation and their environs.

There is a continuing need for improvements in radiation thermometry or in devices which can quickly, accurately and continuously measure the true or thermodynamic temperature of remote objects, either incandescent or at ambient temperatures, of various types without undue complications. Many manufacturing industries could improve efficiency, product or production quality and consistency, and save energy by more precise and accurate control of temperature at various stages in the process. While pyrometers and other radiation measuring devices have sometimes been employed, there are several factors which limit the usefulness of these devices.

It is well known that the measurement of a thermodynamic temperature by non-contact radiation thermometry requires knowledge of the spectral emissivity of the object. Emissivity, which is a function of both temperature and wavelength, is traditionally measured by comparing the emittance of a radiating body to that of a black-body at a given wavelength and temperature. In addition, however, emissivity is dependent upon the optical or surface characteristics of the object, which may vary from one location on the object to another, or which may vary over a period of time. Factors which can affect the spectral emissivity include the degree of surface roughness, the chemical nature of the surface, and the environment, finally, its intrinsic optical properties. These factors cannot be estimated reliably, calculated from known principles, or compensated for by traditional or known methods. Also, background radiation, i.e., radiation from sources other than the object being evaluated, may result in measurement errors of brightness, since the radiation may enter the detector, and the object may appear brighter than it actually is.

In view of the above, the measurement of the thermodynamic temperature of radiating surfaces by noncontact radiation thermometry must incorporate spectral emissivity data. Any method which does not incorporate such data together with radiance brightness measurement is prone to large errors, particularly when the surface emissivity is not known or changes with time or temperature.

In summary, major shortcomings in this field in the past have been the inability to compensate for variations of reflectivity and/or emissivity of the object and variations in background radiation.

SUMMARY OF THE INVENTION

In accordance with the present invention, the thermodynamic temperature of a remote object, especially an incandescent object is determined by the simultaneous or concurrent and in situ measurement of emissivity and brightness temperature. The apparatus and method uses a single apparatus for both measurements, with the resulting data being fed to an appropriate computer for essentially instantaneous and accurate determination of the thermodynamic temperature, optical constants and other values.

The apparatus and method of the present invention involves the measurement of a change in polarization on reflection of light from a sample surface. By measuring the amplitude and phase change of light polarized both parallel and perpendicular to the plane of incidence, one obtains a precise measurement of the following: (i) spectral reflectivities, (ii) spectral emissivities, and (iii) the optical constants of the surface such as dielectric constants and refractive indices. A simultaneous measure of the radiation emitted by the object at the same wavelength then provides the absolute thermodynamic temperature with a high degree of accuracy.

Preferably, the apparatus employs a light source, such as a laser, of known polarization and wavelength, which is reflected off the sample at an angle in the manner of a probe and is received by a detector means. Other types of intense light sources may be employed, such as a Nernst glower, xenon arc or other gases at high and low pressures. The detector means includes a primary beam splitter means for dividing the amplitude of the radiation into two components of reflected and transmitted radiation. These two components are further subdivided into two components each, to completely analyze the polarization states of the transmitted and reflected beams. The intensities of the four beams are independently measured by four separate detectors.

The light source may be turned on and off very rapidly or modulated in a continuous fashion. This provides two different sets of data from the four detectors. In the alternative, the modulator may be omitted, and the brightness temperature may be measured by a separate detector.

The values at the detectors are employed to determine the dielectric constants and hence the refractive index and reflectivity, and further, the precise instantaneous emissivity of the sample. The degree of polarization of emitted light may be measured by the polarimeter. Further, the degree of polarization may be calculated from measured optical properties. Comparison of the two enables corrections for background radiation.

In addition, the sum of the intensities of self-emittance at all four detectors may be used to determine the brightness temperature, which may be first calibrated against a source of known temperature. The values at the detectors also correspond to the four Stokes vectors of the source, which are a measure of the degree of polarization associated with the sample. If there is a hot background such as the walls of a radiant furnace, an extra depolarization is introduced into the emitted light, and this may be calculated to reject such extraneous factors. Determination of the brightness temperature and the precise instantaneous emissivity allows calculation of the thermodynamic temperature.

The method and apparatus of the present invention allow instantaneous, precise measurements of the thermodynamic temperature of virtually any sample and, in addition, enable one to reject interference from surface roughness effects and hot backgrounds such as furnace walls. The invention may be employed over a temperature range of 300K and lower and up to 3000K or higher by suitable choices of detectors and operating wavelengths. In addition, the method and apparatus can provide values of optical constants such as the dielectric constants, refractive indices and spectral emissivities and reflectivities of the material in question at various wavelengths and temperatures.

DESCRIPTION OF THE PREFERRED EMBODIMENTS

Figure 1:
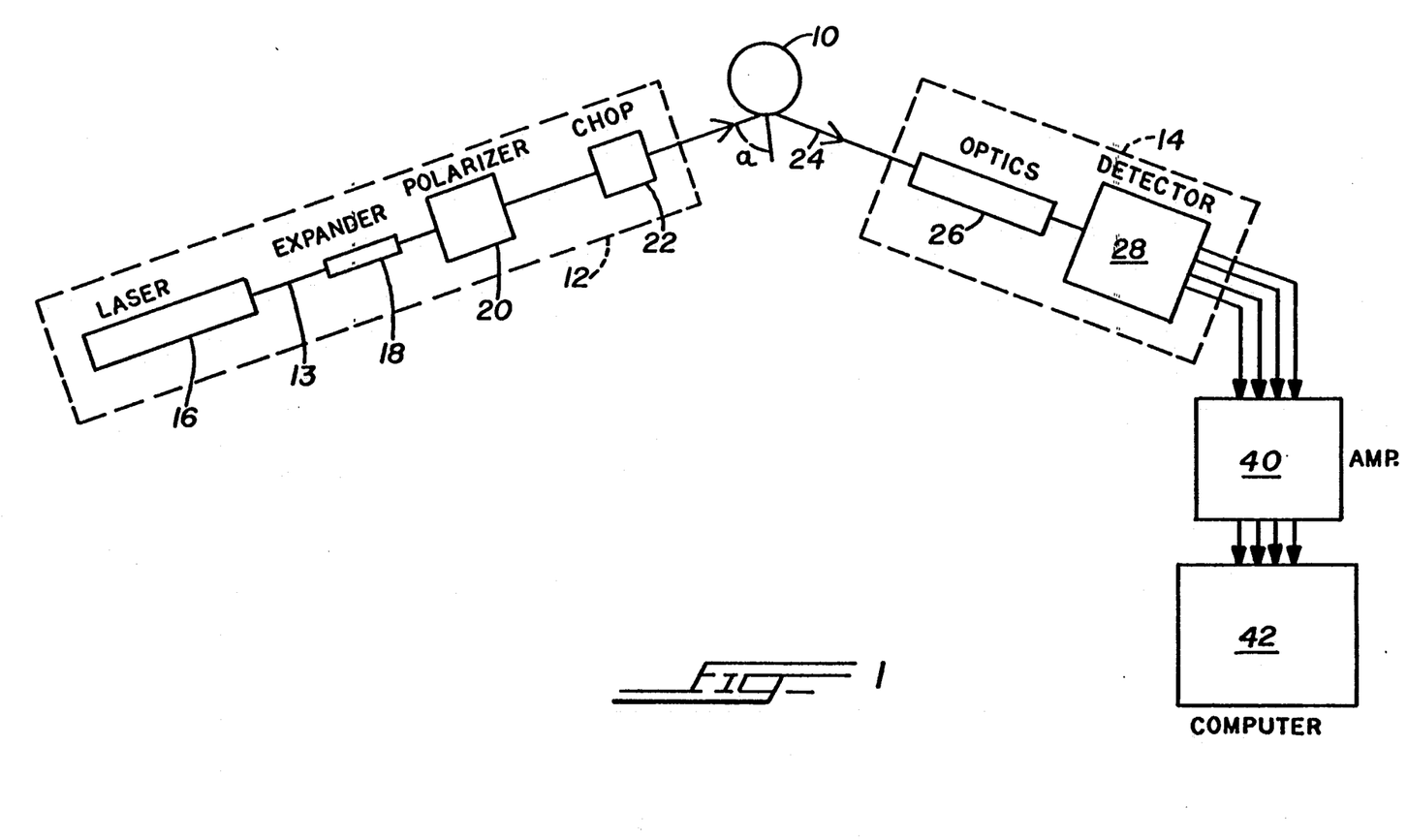
FIG. 1 is a schematic view of the overall apparatus of the present invention.

FIG. 1 is a schematic representation of the apparatus of the present invention, which is used to measure the thermodynamic temperature and other properties of a sample 10. While the apparatus is shown as a series of components, all of the components, with the exception of the electronics and computer may be, with no moving parts.

The sample 10 is shown as round for the purpose of illustration only. The sample may be of any size or shape, specular or partially diffuse, liquid or solid, and may be at a temperature of from about room temperature to 4000° K. or above, although the most useful operating range for practical purposes in the order of about 500 to 4,000° K.

The device comprises two major subassemblies, indicated within the dotted line boxes at 12 and 14. Preferably, the subassemblies 12 and 14 are connected or secured together in a fixed angular relation, as will be described herein in more detail.

The subassembly 12 includes a light source, preferably a laser 16 operating at a given frequency, for example, a helium-neon laser. The intensity of the laser light must be sufficient to carry out the reflection measurements as herein described.

The light beam 13 from the laser 16 is aligned with, and passes through an expander 18 and thence a polarizer 20. The polarizer is oriented to provide a desired polarization state, for example, that is linearly polarized at 45° with respect to the plane of incidence. The polarized laser light passes through an electro-optic modulator 22, aperture, or other device, such as a mechanical chopper, which rapidly opens and closes on a continuous and regular basis. The light is then directed to be incident at an angle (a) with the surface of the sample 10, and is reflected at the same angle (a) on a line 24 into the aligned detector subassembly 14.

It will be noted that when the laser light is interrupted or off, the detector means 14 will receive radiation on an angle that is self-emitted from the sample. When the laser light is on, both the self-emitted radiation and the reflected radiation from laser 16 are collected by the detector means 14. The rapid on-off cycle of the laser light enables discrimination between reflected light and the self-emitted light during the measurements.

The detector means 14 may include a front portion 26 comprising suitable lenses and adjustable mirrors to focus and adjust the reception of the polarimeter. The detector itself, 28, is shown in more detail in FIG. 2.

Figure 2:
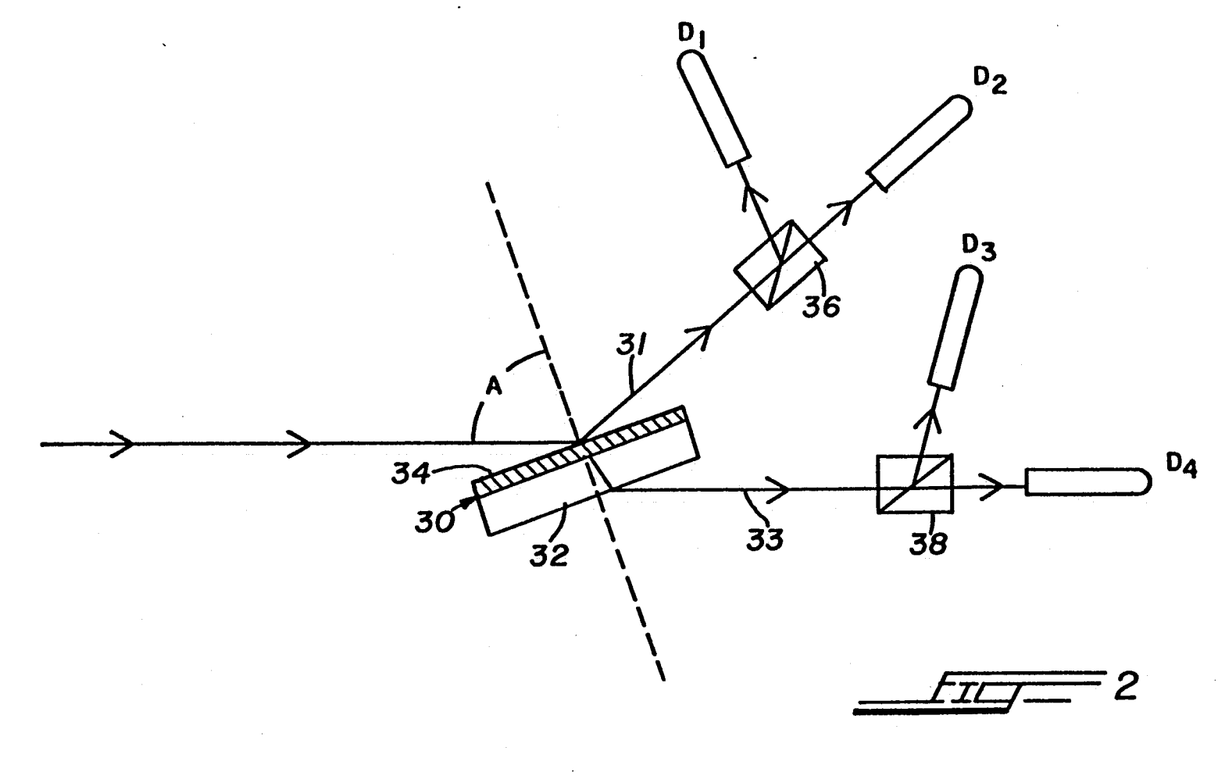
FIG. 2 is a schematic view of the detector system of the present invention.

As shown in FIG. 2, the detector comprises a beam splitting means 30 to effect amplitude division and phase shifting of the radiation from the sample into reflected and transmitted components, 31 and 33, respectively. The beam splitter 30 may comprise, for example, a substrate 32 coated with a dielectric 34 designed for a particular wavelength. For example, a suitable beam splitter may be composed of zinc sulfide with a magnesium fluoride coating of 78.2 nm thickness on the beamsplitting face for the He-Ne laser wavelength of 0.6328 mu m. Suitable beam splitters at other wavelengths can also be designed. The angle of incidence (A) is about 70°, and the beam splitter would be a slab of sufficient thickness or curvature to enable removal of multiply internally reflected beams. Consequently, a curved beamsplitter and a different angle of incidence could be used.

Each of the divided beams 31 and 33 are then divided into their polarization components by the separate means indicated at 36 and 38. For example, 36 and 38 may comprise two beamsplitting polarizing prisms, such as Glan-Thompson prisms, which analyze the reflected and transmitted beams from the splitter. There is a significant difference in polarization states of the reflected and transmitted beams, and such a change provides the basis for complete characterization of all four Stokes vectors.

Also, as shown in FIG. 2, the intensities of the resulting four beams of radiation are measured by four detectors $D_1$, $D_2$, $D_3$ and $D_4$. The detectors are chosen for the particular wavelength being employed. For example, silicon photodiodes may be employed for wavelengths from visible to near infrared. As explained previously, two separate readings are obtained from each of the detectors: one when the laser is on, and the other when the laser is off. Referring again to FIG. 1, the values from the detectors may be collected by suitable devices, such as lock-in amplifiers or phase sensitive detectors, generally indicated at 40, and fed into a suitable high-speed data gathering and processing system 42 to perform the necessary calculations and output.

The readings from sensors may be used to calculate brightness temperature, emissivity, and hence the true thermodynamic temperature of the object. Also, since the device is a complete polarimeter, with the four values corresponding to the four Stokes vectors, factors such as surface roughness and background radiation can be accounted for, in order to allow a more accurate determination of the thermodynamic temperature. Since the laser is modulated at a high rate, the alternative readings in the on and off state are obtained instantaneously and continuously.

In order to use the device accurately, it is desirable to make certain calibrations. With the laser off, the brightness temperature measurement, or sum of intensities on all four detectors $D_1$ to $D_4$, may be calibrated by comparison with a similar heated object of known temperature.

For measurement of the Stokes vectors from the intensities on the detectors, it is necessary to determine a matrix by calculation but preferably by calibration. The calibration may be accomplished by deliberately polarizing the light incident on the detector means into four independent known states using a polarizer and compensator combinations. The intensities measured at the detectors (four times) are sufficient to calibrate the entire matrix.

Figure 3:
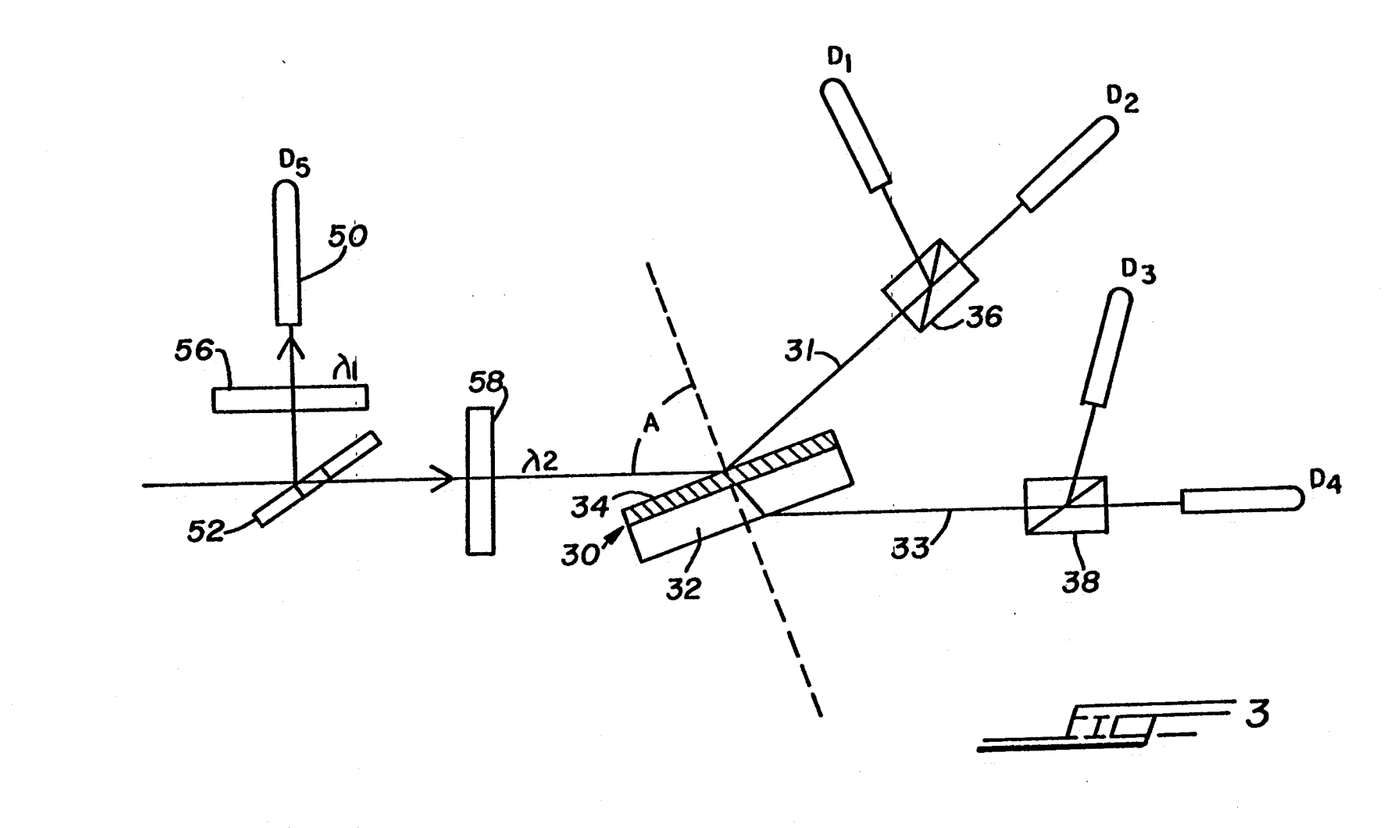
FIG. 3 is a schematic of another embodiment of the apparatus of the present invention.

FIG. 3 illustrates another embodiment in which the need to use a chopper or a like device to turn the laser beam on and off the sample is eliminated. The same polarimeter is employed as shown in FIGS. 1 and 2 and except as otherwise noted, the parts are identical and carry the same reference numerals.

In the present embodiment, an additional detector 50, indicated as $D_5$, is employed to make the brightness temperature measurement. The detector $D_5$ is positioned away from the other detectors. A beam divider 52 or a reflector with a small aperture is placed in the path of the beam from the sample. The laser light reflected from the sample continues in a straight line through the aperture into the polarimeter for analysis by detectors $D_1$, $D_2$, $D_3$ and $D_4$. The self-radiation from the sample is substantially reflected into detector $D_5$. This allows the simultaneous measurement of the brightness temperature at $D_5$ and the emissivity at $D_1$–$D_4$ and hence the simultaneous determination of thermodynamic temperatures.

It will be understood that the detector $D_5$ could be placed at any predetermined angle, such as at normal incidence, at any convenient location outside of the device housing the other sensors.

Figure 4:
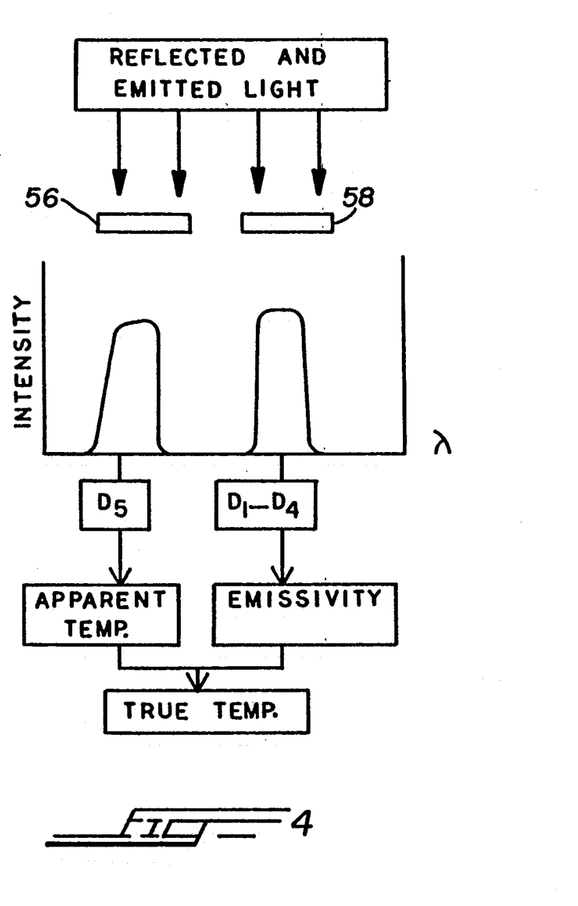
FIG. 4 is a schematic illustration of an embodiment using slightly different wavelengths of light for the embodiment shown in FIG. 3.
Figure 5:
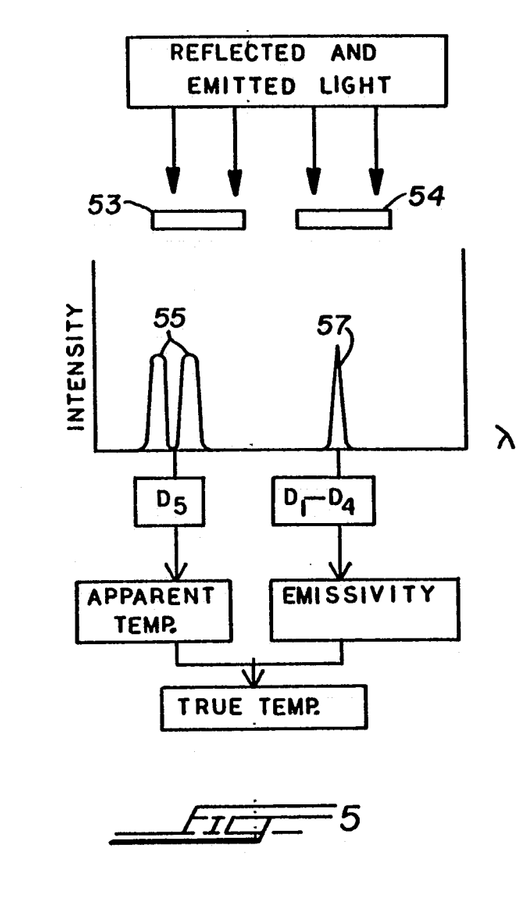
FIG. 5 is a schematic illustration of another embodiment using a filter for some of the detectors.

FIGS. 3, 4, 5 and 6 show the possibility of using various types of filters in conjunction with one or more of the various radiation beams which are being analyzed. FIG. 5, for example, shows the use of a wide bypass filter elements 53 and 54 to allow a broader spectrum of light 55 to reach the detector $D_5$ than $D_1$ to $D_4$, in order to increase the sensitivity of the brightness temperature measurement while excluding the frequency 57 of the relatively intense laser light which goes to the polarimeter detectors $D_1$ to $D_4$.

As shown in FIGS. 3 and 4, the filters 56 and 58 may be employed to pass light to the respective detectors at slightly different frequencies to eliminate possible interference from one measurement to the other. The frequencies are sufficiently close so that no significant error is introduced into the system.

Figures 6, 7, 8:
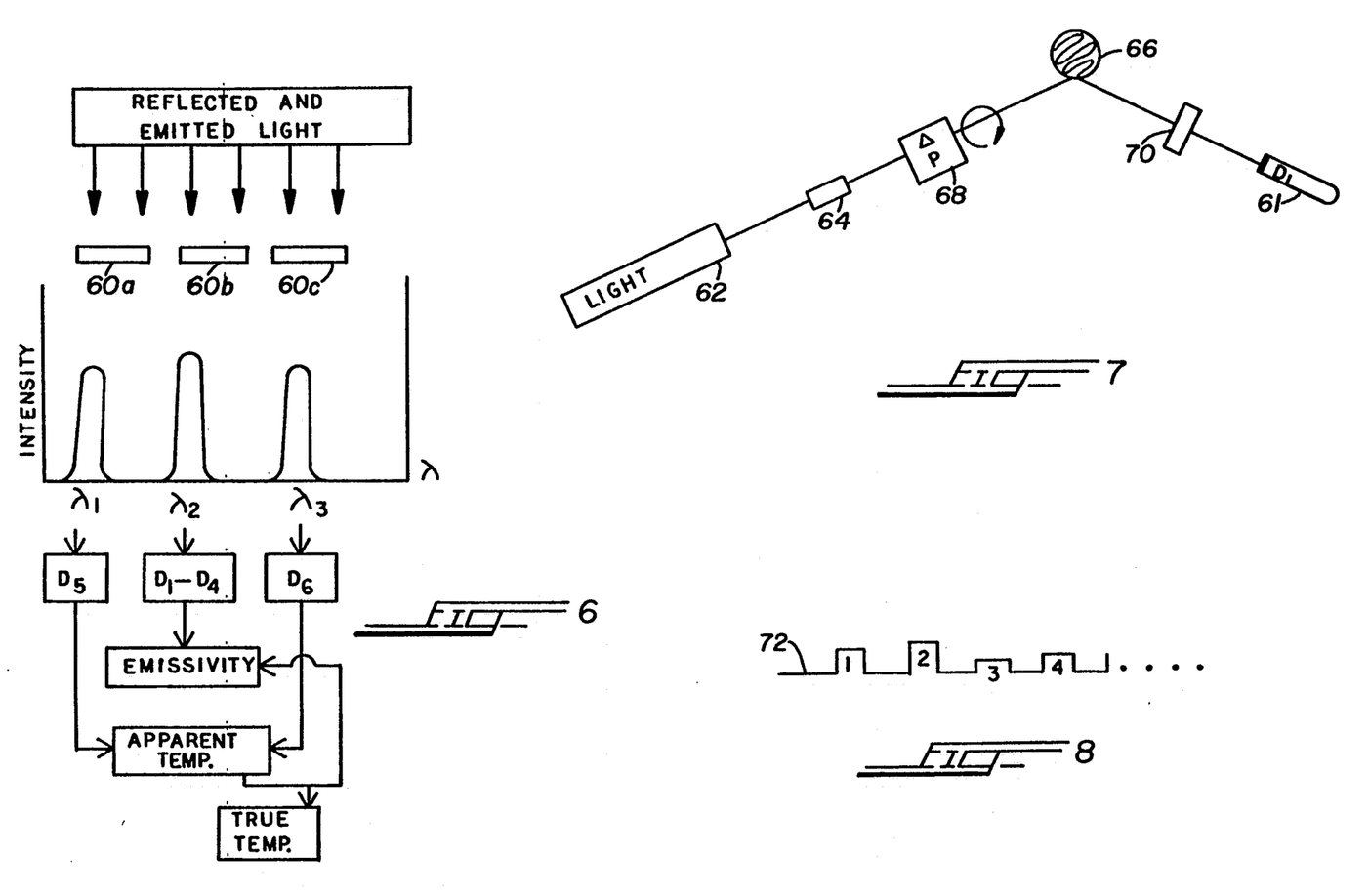
FIG. 6 illustrates the use of another type of filter in connection with the present invention.
FIG. 7 is a schematic illustration of yet another embodiment of the present invention.
FIG. 8 is a schematic illustration of the data gathered from the embodiment of FIG. 6.

In FIG. 6, the filter has three elements 60a, 60b and 60c in a narrow band width to allow passage of the laser light 2 through the center element 60b for t analysis by detectors $D_1$–$D_4$, while allowing radiation from the object 1, and 3 to pass through the other elements 60a and 60c for measurement by detectors $D_5$ and $D_6$. The values at $D_5$ and $D_6$ are added to determine brightness temperature.

FIGS. 7 and 8 illustrate the possibility of using a single detector 61 ($D_1$) and making a series of measurements to obtain the same values of the devices shown in FIGS. 1 to 3. In the present embodiment, light from a source such as a laser 62 is passed through a chopper 64 and is reflected from the sample 66 toward the detector 61. Prior to reaching the object, the laser beam is passed through a rotatable polarizer, such as a polarizing prism 68. The prism 68 is rotated into four successive positions to change the plane of polarization of light. The light reflected from the object 66 also passes through a fixed polarizer 70 before reaching the detector 61.

At each of the four rotary positions of the polarizer, the laser light is turned on and off to obtain readings such as those schematically shown in FIG. 7. The baseline 72 corresponds to the brightness temperature when the laser is off, and the numbered values correspond to the four separate and sequential readings when the laser is on. These, in turn, correspond to the four Stokes vectors mentioned previously, which allow calculation of emissivity and the other essential values.

Figure 9:
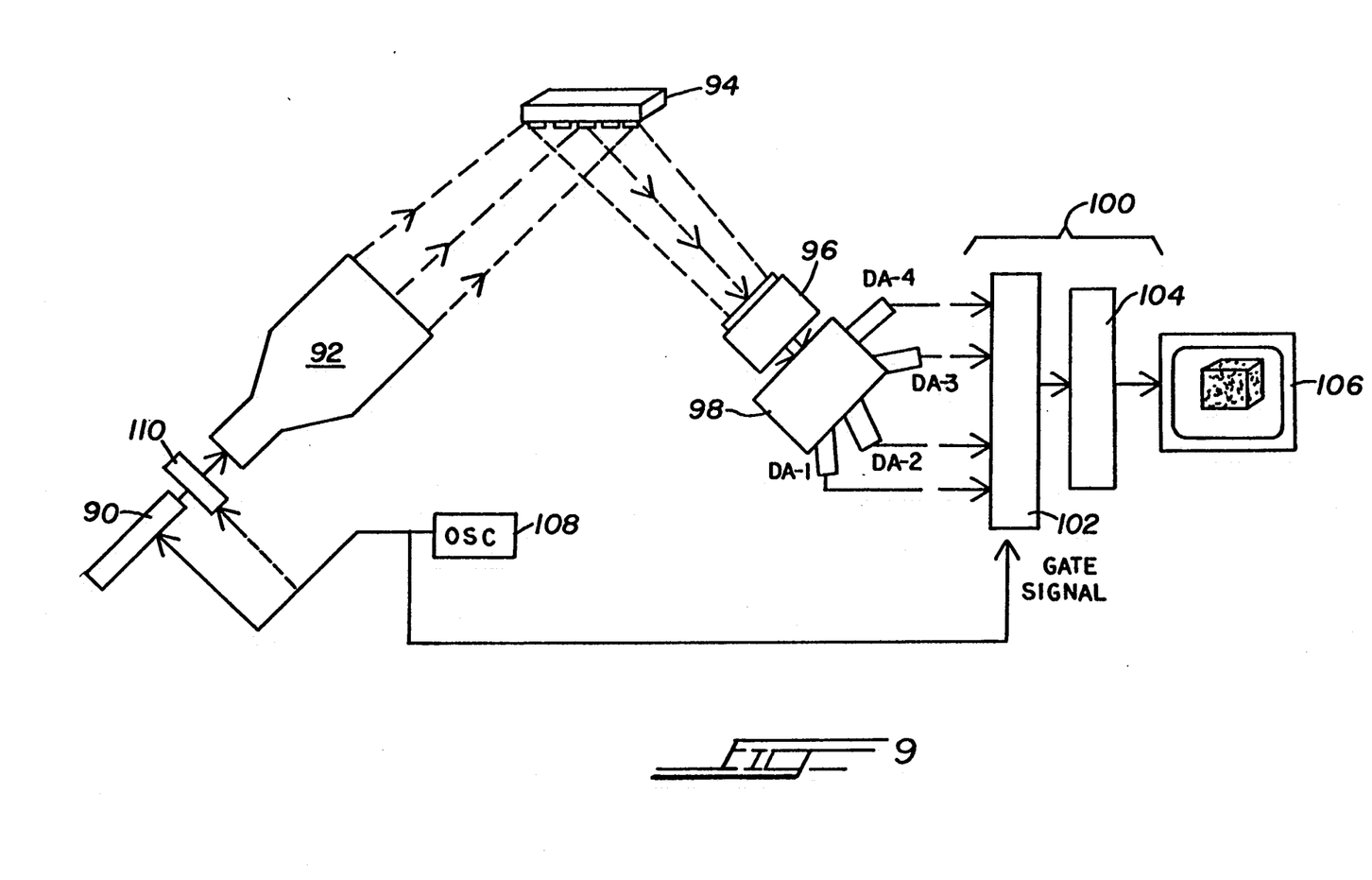
FIG. 9 is a schematic of an alternate detector means to enable thermal imaging.

Using the same basic apparatus previously described herein, it is also possible to provide detailed analysis or image over an entire surface area of an object, as contrasted with a single spot impinged by the laser beam in the previous embodiments. Such a device might be useful, for example, for nonobtrusive testing or evaluation of various articles such as integrated circuits having a large number of components. In FIG. 9, light from laser 90 is directed to a beam expander 92 so that the laser light floods the entire area of the remote object 94. The laser light is then reflected from various positions on the object 94 and is collected by the collecting optics 96. The reflected light, after collection, is analyzed in a way described previously for the polarization analyzer 98. The analyzer 98 comprises a similar set of prisms and detecting elements $D_1$–$D_4$ as shown earlier in FIG. 2. These detecting elements (D.A. 1-4) in this case, however, consist of arrays of photo sensitive detectors, for example, like those in charged coupling devices (CCD) commonly used in solid state video cameras, or other such arrays of multiple elements of photo detectors. With careful alignment of the optic system, light from each position on the object now goes to a unique detector element in each of the four detector arrays. The amplitude information from every element of each array is then transmitted into an appropriate data acquisition system 100. Each of these signals may be analyzed by an analog to digital converter 102 and the corresponding amplitudes from each point on the object would be treated computationally as if they can from the detectors $D_1$–$D_4$, as was the case shown in FIG. 2 for a single spot, optical temperature measuring device. These amplitudes are then used by the computer 104 in the calculation to find the four Stokes vectors for each point corresponding to the elements in the photo detector array. For instance, a commercial video camera may have 200×300 array positions giving 60,000 separate bits of data in each of the four detector arrays. The computer 104 can then calculate the optical properties of each point separately on the surface of the object and from the calculated emissivity and from the total emitted light from the object, as seen by the four detector arrays, then calculate the true thermodynamic temperature of each of the 60,000 array points which correspond to the various points on the object. This true temperature can then be converted back to an image of the object, color coded on a color monitor 106 for viewing, or otherwise made available for analysis.

In order to simultaneously determine the temperature, the laser may be pulsed or chopped in order to separate in the detector arrays the light which comes from the object alone because of its inherently emitted thermal radiation, and that light which comes by reflection from the laser source. The detector arrays and the operation of the digital to analog converters may be gated by the appropriate pulse generated by the same oscillators 108 which produce the pulsating of the laser 90 or operate an optical chopper 110. In this way the same analysis as previously described can produce the true thermodynamic temperature over an area of an object.

Figure 10:
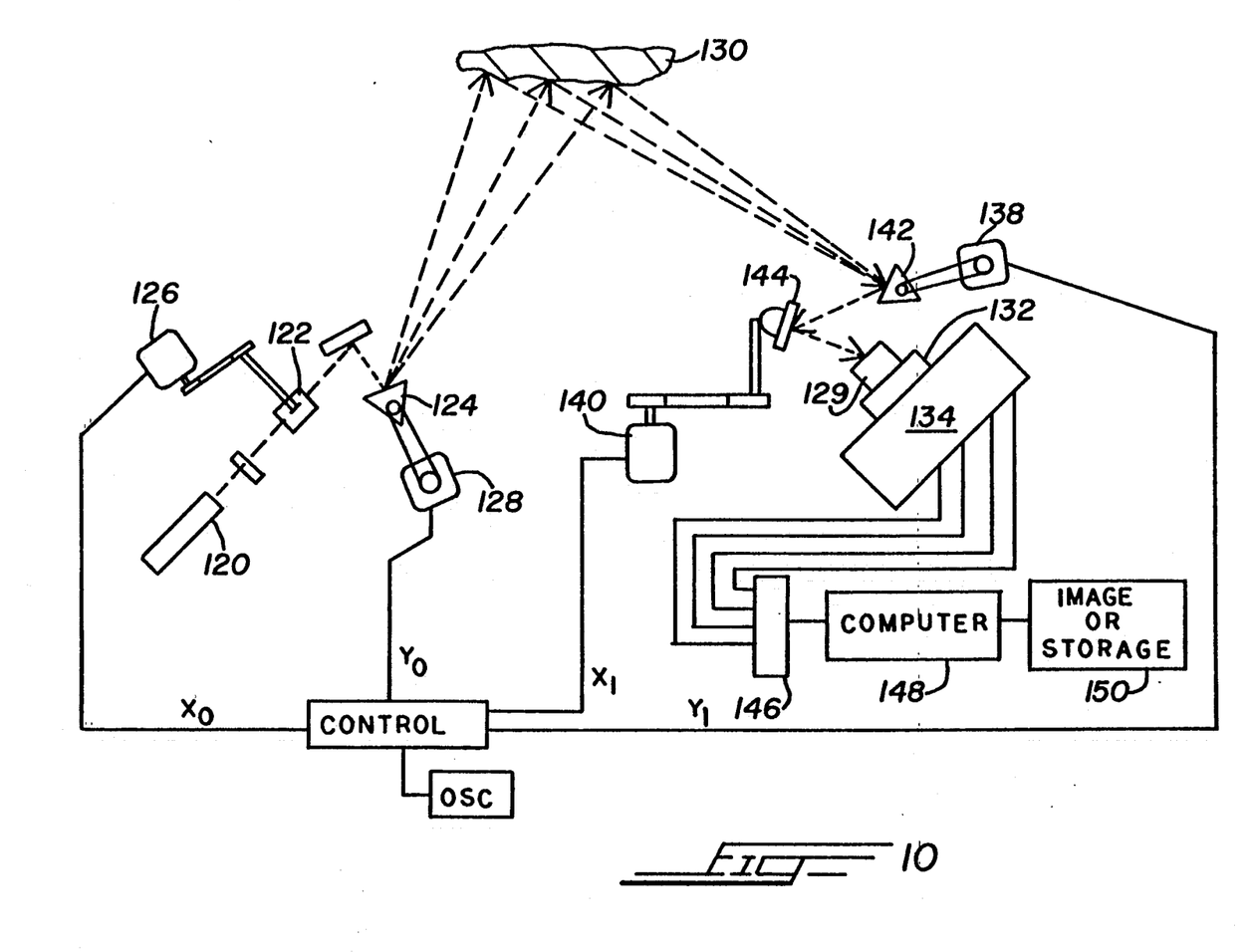
FIG. 10 is a schematic of yet another detector system to enable the scanning of the thermal image of a remote object.

In FIG. 10 another embodiment of this invention is described. Here, the beam from a laser 120 is scanned by rotating mirrors 122 and 124. The mirror 122 is rotated synchronously by stepping motor 126 to scan the laser beam in an $x_o$ direction, but at a substantially different rate. This produces a "raster scan" pattern of laser light onto the remote object 130. The laser light reflected from the remote object 130 is similarly directed into collimator 129 the collecting optics 132 and polarization analyzer 134 which is similar to that shown in FIG. 2. At any given moment, the light from only one small area or spot on the object can get into the collecting optics 132. The controller 136 synchronizes the mirror motors 138 and 140 connected to respective mirrors 142 and 144 in a manner such that the spot on the object reflects light only into the collecting optics 132 along axes $x_1$ and $y_1$ and only at the same time as the laser light is directed onto that spot by mirrors 122 and 124.

Thus, at any moment in the scanning of the light beam, there is laser light landing on one spot on object 130 ad only that spot can reflect light into collimator 129 and the collecting optics 132. The light, after collection, is then polarization analyzed and detected in device 134 by sensors $D_1$–$D_4$ are then sampled in the analog to digital converter 146 and stored by the computer 148 as a function of time which corresponds to the relative position of the laser beam in the raster scan sense. Thus the complete image of the object can be viewed or stored at 150 with the set of the four Stokes vectors known for each point of the scan. This enables the calculation of the true thermodynamic temperature at each point on the object, as well as the optical properties at each point, as in the case of FIG. 9.

In summary, the device of the present invention has no moving parts and has the following capabilities:

1. Measurement of all four Stokes vectors in reflection instantaneously.
2. Determination of optical properties and spectral emissivities.
3. A response time on the order of about 1 microsecond or less.
4. Determination of correction factors for surface roughness effects (depolarization or diffuse reflections).
5. Measurement of radiance brightness temperatures (radiance due to self emission).
6. Prediction of the degree of polarization expected from the self emission of the sample, based on measured optical properties.
7. Measurements of the degree of polarization of emitted light.
8. Comparison of the quantity (7) with that computed in (5) provides an estimate of the total depolarization observed. This would be particularly important in making measurements of a sample's temperature in the presence of an incandescent background such as a radiant wall surface.
9. Using (1) through (8), precisely determining the thermodynamic temperature, with an accuracy of better than two percent over a wide temperature range.

We claim:

1. Method for non-contact determination of the thermodynamic temperature of a remote object comprising the steps of:

a. directing a polarized light beam of a given wavelength toward said object to cause said light to be reflected from the surface of the object along a given plane of incidence,
   b. measuring the amplitude and phase change of light reflected and transmitted from said object of said wavelength polarized both parallel and perpendicular to the plane of incidence to determine the spectral emissivity of the object.
   c. interrupting said polarized light beam and concurrently measuring the self emission of the object exclusive of the reflected light to determine brightness temperature, and
   d. combining the values obtained in b. and c. to determine the thermodynamic temperature of the object.

2. The method according to claim 1, wherein the measurement set forth in step b. is made by four separate detector means.

3. The method of claim 2, wherein the measurement set forth in step c. is made by an additional separate detector means, and the measurements in steps b. and c. are made simultaneously.

4. The method according to claim 1, wherein the light beam is interrupted repeatedly turning said light beam on and off.

5. The method according to claim 4, wherein the measurement in step b. is made when the light is on, and the measurement in step c. is made when the light is off.

6. The method of claim 1, wherein the measurements of steps b. and c. are at slightly different wavelengths.

7. The method of claim 1, wherein the measurement of step b. is made by a single detector means sequentially at four difference polarization states.

8. The method of claim 1 wherein the measurement in steps b, and c, and step d are at a single spot on a surface of said object.

9. The method of claim 1 wherein the measurement of steps b and c, and step d are made at a plurality of points defining an area of a surface of the object to determine the thermodynamic temperature at said plurality of points in order to provide a thermal image of said area.

10. The method of claim 1 further comprising the step of scanning a plurality of points in a surface of said object to determine the thermodynamic temperature at said plurality of points in order to provide a thermal image of said surface.

11. Apparatus for measurement of the thermodynamic temperature of a radiating object comprising
    a light source means of given wavelength for reflecting a beam of light off the object at a given angle,
    means for interrupting said beam of light,
    detector means for receiving radiation from said object comprising both
       the self-emitted radiation from the object when the light is off in order to determine the brightness temperature of the object and
       combined reflected and transmitted radiation from the object when the light source means is on, in order to determine the emissivity of the object.
    said detector means comprising means for amplitude splitting of the received radiation into two component beams,
       means for dividing each of the two component beams into two beams each of polar components, and
       means for measuring the intensities of the four resulting components, said intensities being related to the four Strokes vectors of the received radiation, and computing means for computing the brightness temperature and emissivity of the object and for combining said brightness temperature and said emissivity to determine the thermodynamic temperature of the object.

12. The apparatus of claim 11 further comprising filter means for discriminating between the self-emitted light and the reflected and transmitted light.

13. The apparatus of claim 11 further comprising means for making simultaneous measurements of the thermodynamic temperature at a plurality of points in a surface of said object in order to provide a thermal image of said surface.

14. The apparatus of claim 13 wherein said means for making simultaneous measurements of the thermodynamic temperature at a plurality of points in a surface of the object comprises means for subdividing the reflected, transmitted, and self-emitted radiation light from said plurality of points defining an area of the object surface.

15. The apparatus of claim 13 wherein the means for making simultaneous measurements of the thermodynamic temperature at a plurality of points in a surface of the object comprises means for scanning said surface.

16. Method for non-contact measurement of the thermodynamic temperature of a remote object, said method comprising the steps of reflecting a beam of light of known frequency and polarization off the object at a given angle, arranging a detector to receive radiation of said known frequency and at said given angle, amplitude splitting of the radiation received by said detector followed by division of the split beam into four polarization components, alternatively interrupting said beam of light while measuring the intensities of said four components to obtain four values for two states wherein one state comprises both transmitted and reflected radiation and the other state is self-emitted radiation; and irrespective of order, calculating the brightness temperature of the object from said self-emitted radiation intensities and emissivity of the object from said transmitted and reflected intensities, and combining these to determine the thermodynamic temperature of the object.

17. Method for non-contact determination of the thermodynamic temperature of a remote object, said method comprising the steps of directing a polarized light beam to the object causing said light to be reflected and transmitted from said object, measuring four polarization components of the light reflected and transmitted from the object to determine emissivity, interrupting said polarized light beam and simultaneously measuring the brightness temperature of the object from radiation self-emitted from the object, and combining the two measurements to determine the thermodynamic temperature.

* * * * *